United States Patent
Stennert et al.

(10) Patent No.: US 6,217,613 B1
(45) Date of Patent: Apr. 17, 2001

(54) PRESSURE-EQUALIZING DEVICE AS A PROSTHETIC REPLACEMENT FOR A EUSTACHIAN TUBE

(76) Inventors: Eberhard Stennert, Othegravenstrasse 1, 50935 Köln; Martin Walger, Brentenstrasse 22, 50354 Hürth; Hartmut Meister, Longericher Strasse 31, 50739 Köln, all of (DE)

( * ) Notice: Subject to any disclaimer, the term of this patent is extended or adjusted under 35 U.S.C. 154(b) by 0 days.

(21) Appl. No.: 09/341,738
(22) PCT Filed: Jan. 10, 1998
(86) PCT No.: PCT/DE98/00072
  § 371 Date: Jul. 13, 1999
  § 102(e) Date: Jul. 13, 1999
(87) PCT Pub. No.: WO98/30183
  PCT Pub. Date: Jul. 16, 1998

(30) Foreign Application Priority Data
Jan. 13, 1997 (DE) .............................. 197 00 814

(51) Int. Cl.[7] ...................................................... A61F 2/18
(52) U.S. Cl. .............................................................. 623/10
(58) Field of Search ............................... 623/12, 10, 902, 623/909, 23.64; 604/8, 264; 607/136, 137

(56) References Cited

U.S. PATENT DOCUMENTS 3,635,798 * 1/1972 Kirkham et al. ................... 195/103.5
4,645,504 * 2/1987 Byers .................................... 623/10
4,969,900 * 11/1990 Fleischer .............................. 623/10
5,499,970 * 3/1996 Olson .............................. 604/264 X
5,865,183 * 2/1999 Hirschebain ......................... 128/864

FOREIGN PATENT DOCUMENTS

47712 * 12/1977 (SU) .

* cited by examiner

Primary Examiner—Michael J. Milano
Assistant Examiner—Brian Pellegrino
(74) Attorney, Agent, or Firm—Trexler, Bushnell, Giangiorgi, Blackstone & Marr, Ltd.

(57) ABSTRACT

A pressure compensation device for a prosthetic substitute of a eustachian tube has an outer part and an inner part. The outer part serves for the admission of air from the outside and has a freely accessible area laterally surrounded by skin. Further, the outer part is provided with a seat for receiving a filter. This filter is accessible from the outside and keeps away coarse dirt and water. The outer part and the inner part are interconnected by a first tube. The inner part has a sealed housing divided into two chambers, namely an outer chamber communicating with the first tube and an inner chamber. These chambers are separated by either a fine filter or by a pressure compensation membrane to assure a germ tight separation. The inner chamber is connected with a second tube ending in a middle ear.

8 Claims, 2 Drawing Sheets

PRESSURE-EQUALIZING DEVICE AS A PROSTHETIC REPLACEMENT FOR A EUSTACHIAN TUBE

BACKGROUND AND SUMMARY OF THE INVENTION

The invention relates to a pressure compensation device that may be implanted as a prosthetic substitute for a eustachian tube.

Various diseases or malformations may be the cause that the middle ear is not ventilated enough by the eustachian tube. Patients with chronic otitis media, chronic bone suppuration, cholesteatoma or middle ear malformations often need to have the eustachian tube replaced by a corresponding prosthesis. Said prosthesis has to assume the pressure compensation otherwise provided by the eustachian tube. Such a pressure compensation device is particularly necessary with middle ear prostheses. Reference is made to the application of the same applicant filed on the same date with the title "Middle ear prosthesis". The content disclosed in said application is included in the content disclosed in the present application.

WO-A-9310729 discloses a prosthetic substitute for the eustachian tube. It describes a ventilation tube designed as a pressure compensation device for the middle ear. The ventilation tube comprises outer parts, inner parts and filter parts that are tightly connected to one another. The inner part is solidly screwed into the cranial bone. The outer part is tightly screwed on the inner part. The filter part may be plugged onto the outside located end of the outer part. The outside located side of the filter part is provided with a filter that is air-permeable but that is sealed against germs, water and the like, said filter being oriented towards the outer world.

This filter part being located outside also has to prevent the middle ear from getting soiled by dust, sand, water and the like. Its filter effect is coarse in order to protect the middle ear against infections by germs. In order to be able to protect it against water and germ penetration, the filter part has to be extremely fine pored. Due to the outside location of the filter part, the very fine pored filter runs high risks to get obstructed by coarse particles such as dirt or dust.

The object of the present invention is to provide a pressure compensation device that replaces the natural eustachian tube when latter is not able to ventilate the middle ear, whereas simultaneously the service life of the filters used and the sterility of a possible change of filter are to be improved.

The solution of this object is to provide a pressure compensation device as a prosthetic substitute for a eustachian tube with an outer part and an inner part that are tightly connected via a first tube, whereas the outer part 1. may be anchored in a bone and has a freely accessible area compared with the surrounding skin, 2. has a seat for a filter being accessible from the outside and 3. is provided with an inside connection for the first tube and whereas the inner part has a sealed housing divided into two chambers, namely into an outer chamber and an inner chamber separated from each other either by a fine filter or by a pressure compensation membrane, the outer chamber communicating with the first tube via a connection and the inner chamber being connected via a connection with a second tube ending in the middle ear.

Thanks to the pressure compensation device according to the invention, the ventilation of the eardrum, that is of the middle ear, from a head area accessible from the outside is possible. To that purpose, the outer part is inserted into the bone and is laterally surrounded by skin so that it projects outwards, being thus accessible from the outside. The technique used therefor is quite similar to the one used for bone implanted hearing aids. The outer part is preferably arranged behind the ear and covered as best as possible by the ear concha.

The outer part serves for the admission of air as well as for keeping away coarse dirt and water from the other parts of the pressure compensation device. It is therefore equipped with a filter located in a seat of the outer part and is preferably exchangeable.

The outer part is connected to the inner part via the first tube. The function of the inner part is to assure a germ-tight separation. The inner part has a housing divided into two chambers. These two chambers are either separated from each other by a highly flexible but totally impermeable membrane or they are connected to each other via a fine filter. The two chambers of the housing are designated as outer chamber and as inner chamber, the outer chamber being connected to the outer part via the first tube. The inner chamber is connected with the middle ear via the second tube, preferably with a middle ear prosthesis provided there.

The highly flexible membrane sees to it that no germs coming from the outer chamber may enter the inner chamber. The fine filter has the same function, said filter being additionally air-permeable. In order to provide the fine filter with the biggest possible filter surface, the filter is preferably designed as a hollow fiber filter. With regard to hollow fiber filters overall, reference is made to the U.S. Pat. Nos. 5,108,464 and 5,002,590 and particularly to the literature cited there.

The use of two filters (coarse and fine filter) as claimed in the present invention and more particularly the use of a coarse filter and of a highly elastic membrane protecting the middle ear against dirt and infections has considerable advantages compared with the filter arrangement in pressure compensation devices of the art:

1. The coarse filter located outside is susceptible to obstruction. It may be reached from the outside and is easily exchangeable.

2. The extremely fine pored fine filter arranged in the inner part runs high risks of obstruction by dirt. It is protected against dirt by the coarse filter arranged on the outer part. The obstruction of the fine filter is thus reliably prevented by the outside located coarse filter. The fine filter needs no more to be changed. If, instead of the fine filter, a highly flexible membrane is used for pressure compensation, the problems occurring by obstruction and described above are entirely avoided.

3. The arrangement of the fine filter inside the inner part implanted in the cranial bone protects the fine filter against any mechanical influence and thus against damage.

4. The outer part is connected to the inner part by means of a tube and said inner part is connected to the middle ear by means of another tube. This is of great cosmetic advantage. The tubes and the inner part may be implanted in the cranial bone so as not to be visible from the outside. The outer part may be freely positioned and more particularly implanted so as not to be visible from the outside.

5. As already explained under 2., the separation of coarse and fine filter increases the service life of the fine filter which has no more to be exchanged. When changing the coarse filter, which has to be done from time to time, the fine filter or the membrane always prevent germs to penetrate into the middle ear. As opposed to the pressure compensation devices of the art, the pressure compensation device according to the invention guarantees sterility during a possible change of filter.

Further advantages and characteristics of the invention will become clear in the remaining claims and in the following description of embodiments that are only examples and are not limiting the scope of the invention. Said embodiments are explained in more detail with the aid of the drawing.

DESCRIPTION OF THE PREFERRED EMBODIMENTS

Figure 1:
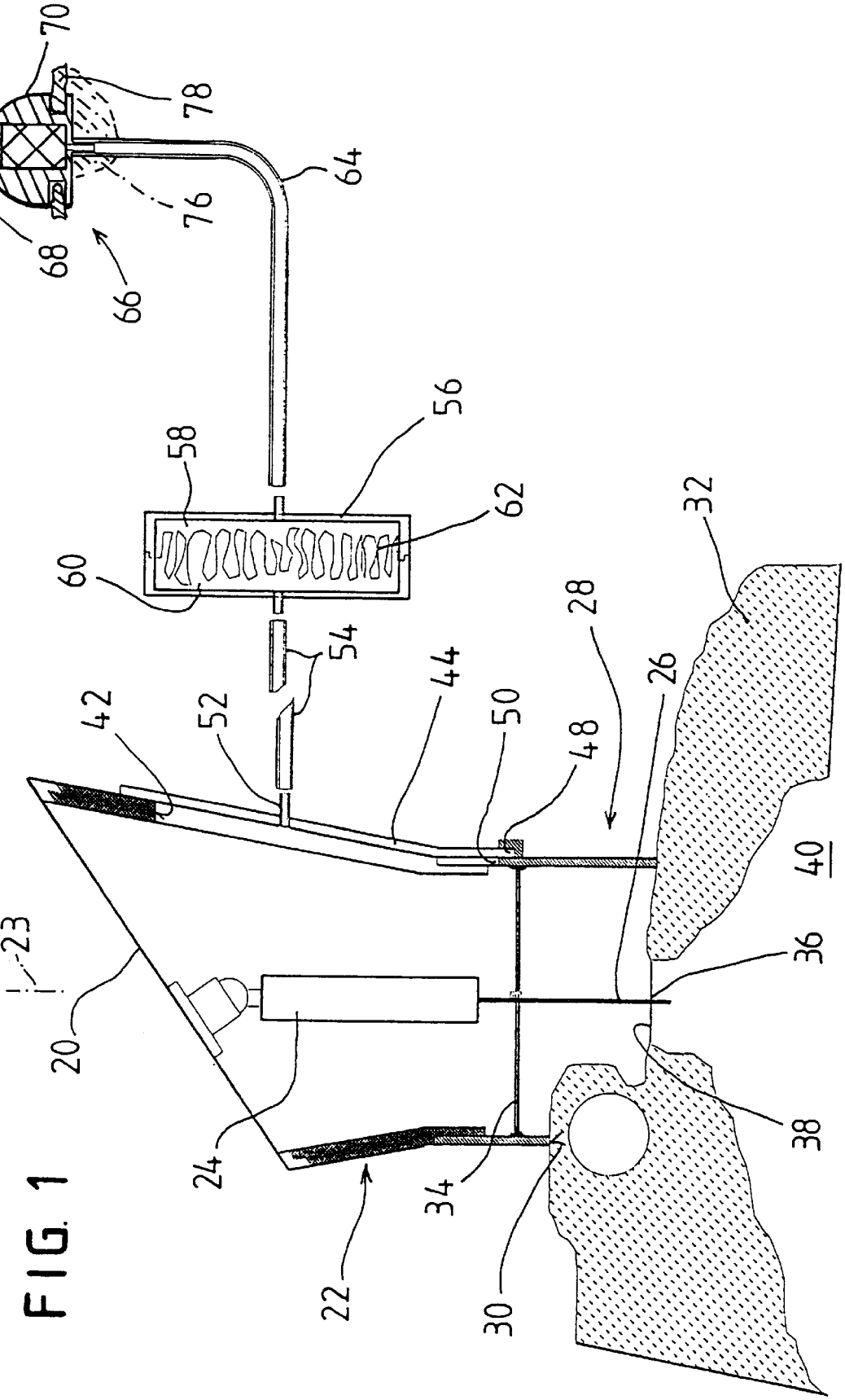
FIG. 1: is a sectional side view of a middle ear prosthesis with the pressure compensation device according to the invention, the pressure compensation device being provided with a highly flexible membrane.

In FIG. 1 a pressure compensation device is represented together with a middle ear prosthesis. Both are described in the following:

The middle ear prosthesis has an artificial eardrum 20 with an essentially oval blank. Its surface is bigger than the surface of a normal human eardrum and is for example 1.5 times bigger. It is made of a material biologically appropriate to the use as a prosthesis.

The eardrum 20 is tightly connected to a housing consisting in two parts. The connection is more precisely achieved by means of a transmission part 22. Said transmission part has essentially the shape of a tube. It has a cylindrical area represented in the lower part of FIG. 1 and an area expanding from said cylindrical area and running on an envelope of cone. The diameter of the cylindrical area is of approximately 6 mm. The expanding area has corresponding measurements of about 11 mm. As may be seen in FIG. 1, the eardrum 20 is located on one level and runs in an angle of 37° to a longitudinal axis 23 of the transmission part 22. Due to the slant position of the eardrum 20, the eardrum 20 has a bigger surface than the normal ear.

A second ossicle part 24 is durably fastened on the inner side of the eardrum 20, preferably in the center of the surface. In the present embodiment, a commercial ossicle substitute of the enterprise Richards GmbH is used. It has a ball-and-socket joint in the vicinity of the eardrum 20. Underneath said ball-and-socket joint a hollow shank receives a first ossicle part that still has to be discussed. The second ossicle part 24 runs underneath the ball-and-socket joint centrically to the center line of the transmission part 22.

The housing also has a coupling part 28. As a whole it is a bit smaller than the transmission part 22 and is designed together with said transmission part in such a way that both parts may be interconnected in an easy, tight and durable way, whereas the interconnection particularly occurs by plugging in longitudinal direction and by gluing. The coupling part 28 is essentially cylindrical. Its diameter is also of approximately 6 mm. It has a free end area 30 having a course imitating as accurately as possible the individual relief of the eardrum wall of a wearer of the middle ear prosthesis. As already explained above, several procedures are available to scan or detect the course of the individual relief of the eardrum wall. Reference is also made in this connection to the patent application "Device for the mechanical scanning and detection of the course of the eardrum wall in a middle ear" of the same applicant and with the same filing date. The disclosure content of this application is included into the disclosure content of the present application.

The free end area 30 is accordingly designed so as to sit close to the eardrum wall 32, as may be seen in FIG. 1. A hermetically sealed closure may thus be obtained at that place. In order to carry through the connection between the free end area 30 and the eardrum wall 32, liquid fastening and sealing material may be used.

In the coupling part 28 a holding device 34 is provided for the first ossicle part 26. Said ossicle part 26 is designed as a thin golden wire that closely fits through a very small, artificial opening 36 in a stapes base plate 38 and that is projecting with its lower, free end area into the inner ear 40. In the embodiment shown, the holding device 34 is an essentially slantways running wire onto which the first ossicle part 26 is fastened or may be fastened. During implantation of the middle ear prosthesis, the holding device 34 is cut through so that the first ossicle part 26 which is connected to the second ossicle part 24 may move freely back and forth through the holding device.

In the embodiment of the middle ear prosthesis as it is shown here, the inner space has to be accessible in order to connect the two ossicle parts 24, 26 and to cut through the holding device 34. Other embodiments without such an access are also possible. A window 42 is provided in the transmission part 22 for said access, whereas the window may be closed by a cover plate 44.

As is shown in FIG. 1, the cover plate 44 has a connection 52. It is assigned for a tube 54. The tube 54 is leading to an inner part of a pressure compensation device. Said inner part 56 is designed as a boxlike housing with two chambers, namely an outer chamber 58 and an inner chamber 60. Both are hermetically separated from one another by a very flexible membrane 62. In another embodiment they are separated from one another by a fine filter 63 that is impermeable to bacteria and microbes, but permeable to air. The fine filters 63 particularly used are hollow fiber filters, see FIG. 3.

The outer chamber 58 is connected to an outer part 66 via another tube 64. It is anchored in a bone 76 and is partially accessible from the outside, see skin 78. The construction used here is similar to the one used in so-called bone-conductive hearing aids. The outer part 66 has a recess 68 into which a filter 70 is inserted. Said filter is preferably exchangeable. The filter 70 hinders water, coarse dirt and so on to permeate into the tube 64. The barrier against germs and the like is achieved by the membrane 62 or by the fine filter replacing it.

Figure 2:
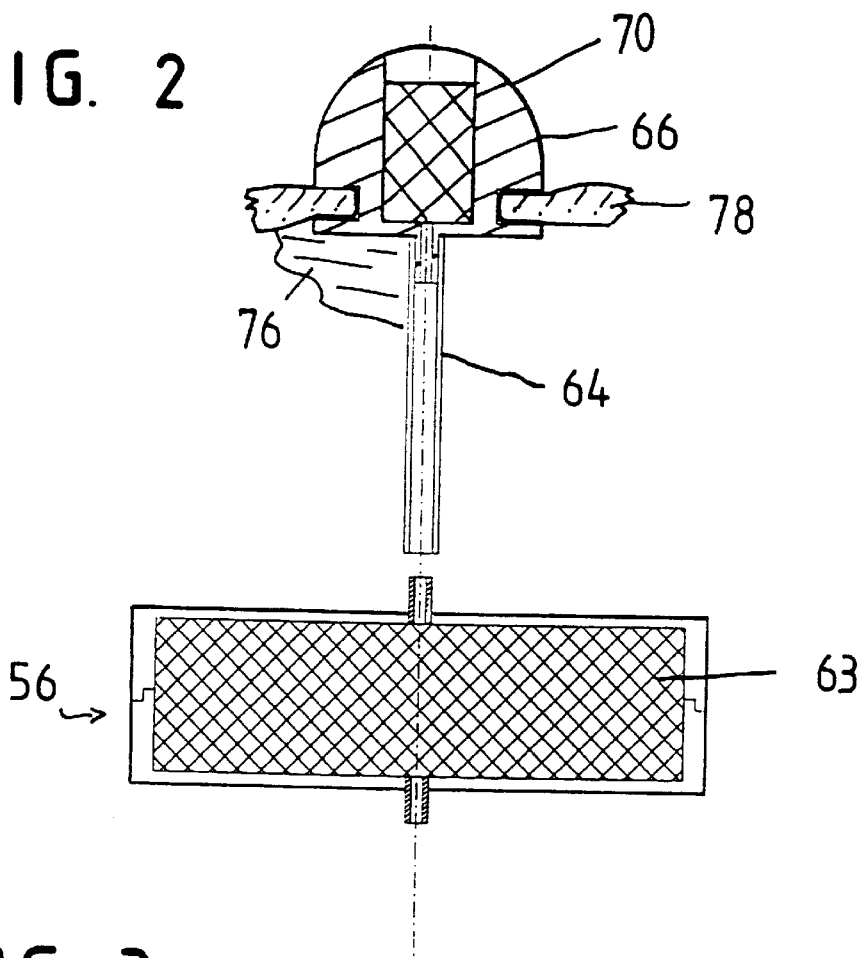
FIG. 2: is a representation of the pressure compensation device according to FIG. 1, but now with a fine filter in the inner part
Figure 3:
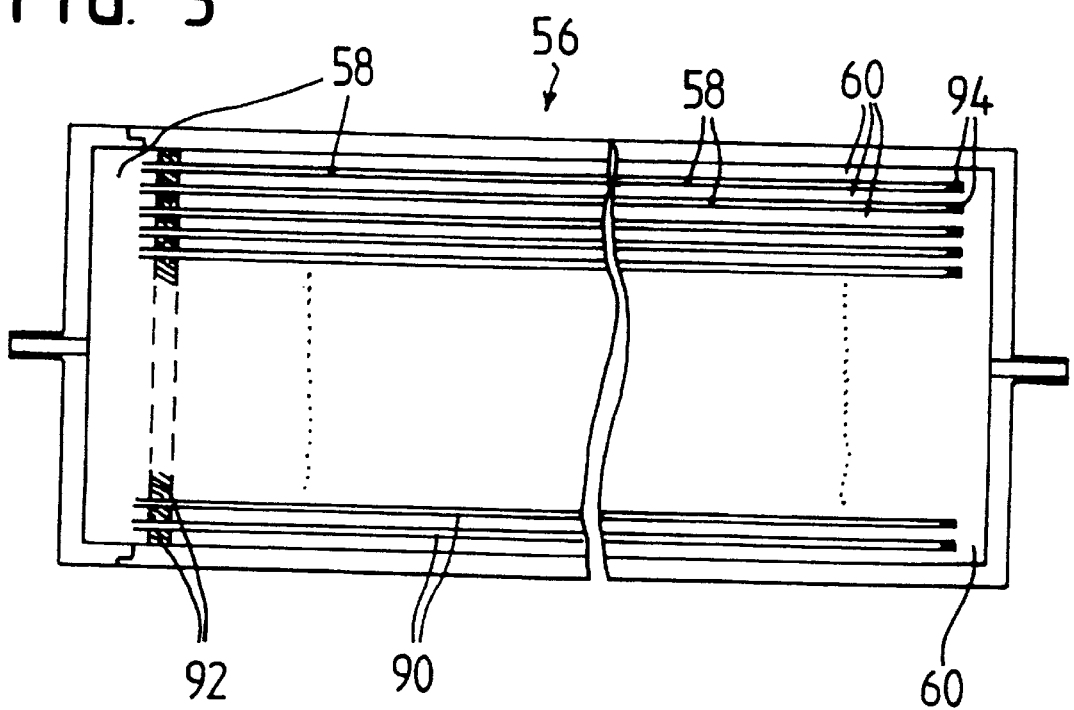
FIG. 3: a sectional representation of an inner part equipped with hollow fibers serving as fine filter.

In the embodiment shown in the FIGS. 2 and 3, the inner part is not provided with a highly flexible membrane 62. The two chambers 58, 60 are separated from one another by a fine filter 63. Said filter is so designed that no germs may permeate from the outer chamber 58 into the inner chamber 64.

Since, after insertion of the prosthesis according to the invention, the inner part is no longer directly accessible and may only be accessed to by another surgical intervention, great importance is attached to the mechanical are for example permanent. The housing of the inner part is permanently hermetically closed. The membrane 62 has a very high resistance. The same is true for the fine filter 63.

FIG. 3 shows an inner part in the housing of which a big number of hollow fibers 90 is arranged. Together they are constituting the fine filter. They are essentially running parallel to one another. They may also sit close to each other, since their circular shape anyway guarantees free spaces between the different hollow fibers. In the representation shown, the free spaces are pertaining to the inner chamber 60. The inner chamber may alternatively also be connected to the inner spaces of the hollow fibers 90. In the drawing according to FIG. 3 the spaces between the different hollow fibers are big in order for the drawing to be better readable. If the hollow fibers 90 should not touch each other, the spacing between them should be kept as small as possible.

FIG. 3 shows that around all the hollow fibers 90 a plug is cast at their left end side so that a free access to their inner spaces is given from the left. The plug 92 tightly coats each of the hollow fibers in the area of their outer sheath and tightly seals the inner wall of the housing.

At its right end side, each and every one of the hollow fibers 90 is closed, for example by dipping it into a corresponding, liquid plastic or by squeezing. In the drawing, this closure is represented by different stoppers 94. They assure that each and every one of the hollow fibers is hermetically closed at its right end side (in FIG. 3).

Membranes for hollow fibers of the type discussed above are known out of the U.S. Pat. No. 4,781,733 as well as of the prior art cited.

What is claimed is:

1. A prosthetic eustachian tube replacing one incapable of fully ventilating a middle ear impaired by disease or malformation, or to ventiltate a middle ear prosthesis, said eustachian tube replacement prosthesis comprising an accessible outer part and a permanently sealed inner part, the outer part being adapted to be anchored in a bone so as to be accessible from outside and partly covered by skin, a filter seat in said accessible outer part, an interchangeable filter means in said filter seat to protect said permanently sealed inner part from water and dirt, said permanently sealed inner part being in the form of a hermetically closed housing adapted for implantation, said housing being divided into two chambers, an air-permeable, but germ-tight means separating the two chambers into a first and second chamber, permitting air flow from the first chamber to the second chamber while restricting the penetration of bacteria and microbes into the second chamber, tube means connecting the accessible outer part and the first chamber of the permanently sealed inner part to permit air flow therebetween, and tube means connecting the second chamber of the permanently sealed inner part with the middle ear to permit air to ventilate said middle ear.

2. The prosthetic eustachian tube according to claim 1, characterized in that the tubes are designed as silicone tubes.

3. The prosthetic eustachian tube according to claim 1, characterized in that the pressure compensation membrane is a thin, tight and highly flexible foil.

4. The prosthetic eustachian tube according to claim 1, characterized in that the housing is essentially boxlike.

5. The prosthetic eustachian tube according to claim 1, wherein the germ-tight means separating the two chambers is a fine filter.

6. The prosthetic eustachian tube according to claim 1, wherein the germ-tight means separating the two chambers is an impermeable membrane.

7. A pressure compensation device for a prosthetic eustachian tube, said device having an outer part and an inner part tightly connected by a first tube, the outer part having a means for anchoring it in a bone and for surrounding it by skin, permitting it to serve for admission of air from outside, the inner part having a means for implanting it in a middle ear, said outer part having a seat for receiving a filter, which filter blocks coarse dirt and water, said inner part having a sealed housing divided into two chambers, namely into an outer chamber and an inner chamber separated from each other in a germ-tight manner by a fine filter or by a pressure compensation membrane, the outer chamber communicating with the first tube and the inner chamber communicating with a second tube ending in the middle ear.

8. A pressure compensation device for a prosthetic eustachian tube, said device having an outer part and an inner part tightly connected by a first tube, the outer part having a means for anchoring it in a bone and for surrounding it by skin, permitting it to serve for admission of air from outside, said outer part having a seat for receiving a filter, which filter blocks coarse dirt and water, said inner part having a sealed housing divided into two chambers, namely into an outer chamber and an inner chamber separated from each other in a germ-tight manner by a fine filter or by a pressure compensation membrane, the outer chamber communicating with the first tube and the inner chamber communicating with a second tube ending in the middle ear, the inner chamber having its fine filter made of a plurality of hollow fibers, which essentially run parallel to one another, which have essentially the same lengths, and which have a closure means at one side end that closes each of the fibers with the other end being tightly encompassed by a plug.

* * * * *